(12) United States Patent
Kubo et al.

(10) Patent No.: US 6,380,168 B1
(45) Date of Patent: Apr. 30, 2002

(54) METHOD FOR PROMOTING HAIR GROWTH

(75) Inventors: Michinori Kubo, Sakai; Masayuki Yoshikawa, Minoo; Hideaki Matsuda, Habikino; Hisashi Matsuda; Toshiyuki Murakami, both of Kyoto; Hiromi Shimada, Toyonaka; Tetsuo Sakurama, Osaka; Manabu Nomura, Miyazaki, all of (JP)

(73) Assignee: Nomura Co., Ltd., Miyazaki (JP)

(*) Notice: Subject to any disclaimer, the term of this patent is extended or adjusted under 35 U.S.C. 154(b) by 0 days.

(21) Appl. No.: 09/611,422

(22) Filed: Jul. 7, 2000

Related U.S. Application Data

(63) Continuation of application No. 09/030,732, filed on Feb. 25, 1998, now Pat. No. 6,297,363, which is a continuation-in-part of application No. 08/661,970, filed on Jun. 12, 1996, now Pat. No. 5,750,107, which is a continuation-in-part of application No. 08/167,828, filed as application No. PCT/JP93/00187 on Feb. 17, 1992, now abandoned.

(30) Foreign Application Priority Data

Mar. 25, 1997 (JP) .............................................. 9-113304
Mar. 25, 1997 (JP) .............................................. 9-113305

(51) Int. Cl.$^7$ ......................................... A61K 31/7042
(52) U.S. Cl. ......................... 514/27; 514/25; 514/880; 424/70.1; 424/74; 424/773
(58) Field of Search ........................... 514/25, 27, 880; 424/70.1, 74, 773

(56) References Cited

U.S. PATENT DOCUMENTS

| 4,175,123 A | 11/1979 | Junge et al. ................. 424/180 |
| 4,376,197 A | 3/1983 | Wallenfels .................. 536/17.4 |
| 5,750,107 A | 5/1998 | Nomura .................... 424/195.1 |

OTHER PUBLICATIONS

The Pharmaceutical Society of Japan1997 Meeting Abstracts, p. 157, abstract No. 27[A5]13–2.
Chernoglazov et al.; "A Method for Detection of Cellulases in Polyacylamide Gels Using 5–Bromoindoxyl–β–D–cellobioside: High Sensitivity and Resolution"; *Analytical Biochemistry*; 1989; 182; pp. 250–252.

*Primary Examiner*—Francisco Prats
(74) *Attorney, Agent, or Firm*—Sheridan Ross P.C.

(57) ABSTRACT

The present invention provides a composition which is useful for promoting hair growth and methods for using the same. The hair growth promoter composition comprises a compound of the formula:

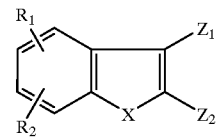

wherein X, $R_1$, $R_2$, $Z_1$, and $Z_2$ are those described herein. Preferably, the compound comprises at least two saccharide moieties.

5 Claims, No Drawings

METHOD FOR PROMOTING HAIR GROWTH

CROSS REFERENCE TO RELATED APPLICATIONS

The present application is a continuation of U.S. application Ser. No. 09/030,732, filed Feb. 25, 1998 now U.S. Pat. No. 6,297,363, which is a continuation-in-part of U.S. patent application Ser. No. 08/661,970, filed Jun. 12, 1996, now U.S. Pat. No. 5,750,107, which is a continuation-in-part of U.S. patent Ser. No. 08/167,828 filed Dec. 16, 1993, now abandoned, which is a United States national phase application based on PCT/JP93/00187, which has a priority date of Feb. 17, 1992. These applications are incorporated by reference herein in their entirety.

FIELD OF THE INVENTION

The present invention is related to a class of novel glycoside indoles. More specifically, the present invention relates to a class of glycoside indoles which are isolated from Calanthe discolor Lindl. and derivatives thereof.

BACKGROUND OF THE INVENTION

The alcohol extract from Calanthe discolor Lindl. is known to be useful for promotion of hair growth and restoration. (JP. A 5-294813) However, the components of this extract have not been identified.

Therefore, there is a need to isolate and identify the active components of the alcohol extract of Calanthe discolor Lindl. There also is a need for compounds that are derivatives of these active components which may be more active and possess other physiological activities.

SUMMARY OF THE INVENTION

The present invention provides a compound of the formula:

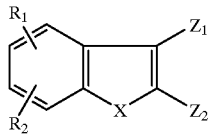

where:
X is O, S, or $NR_3$;
$R_1$ and $R_2$ are independently H, $OR_4$, $SR_5$, $NR_6R_7$, $C_1$–$C_4$ alkyl, or halogen;
$Z_1$ and $Z_2$ are H, $OR_8$, $SR_9$ or $NR_{10}R_{11}$;
$R_3$, $R_4$, $R_5$, $R_6$ and $R_7$ are independently H or $C_1$–$C_4$ alkyl; and
$R_8$, $R_9$, $R_{10}$, and $R_{11}$, are independently H, or a saccharide moiety;
and wherein the compound comprises at least two saccharide moieties.

One embodiment of the invention provides a compound 3-O-β-D-glucopyranosyl (1–6)-β-D-glucopyranosylindole.

Yet another embodiment of the invention provides a compound 2-S-β-D-glucopyranosyl-3-O-β-D-glucopyranosyl-2-mercaptoindole.

DETAILED DESCRIPTION OF THE INVENTION

The present invention is directed to a class of novel glycoside indoles. These compounds have a variety of applications, which include increasing skin blood flow, promoting hair growth and whitening the skin.

More specifically, the present invention comprises a class of chemical compounds described as disaccharide indoles. The compounds of the present invention can be described by general formula I:

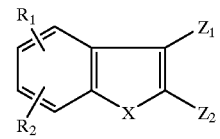

wherein the compound has at least two saccharide moieties. The two or more saccharide moieties can be linked together to form a disaccharide or a polysaccharide chain or they can be attached to different positions of the ring moiety. As used in this invention, a "saccharide" moiety refers to a moiety having one or more carbohydrate moieties. Exemplary carbohydrate includes, glucose, mannose, talose, galactose, allose, altrose, talose, fructose, sorbose, and arabinose. The carbohydrate moiety can be a monosaccharide, disaccharide or a trisaccharide moiety. Exemplary disaccharides include lactose, maltose, cellobiose, and sucrose. The carbohydrate moiety can be in a straight chain form, a furanose form or a pyranose form. In addition, the carbohydrate moiety can be modified such that one or more of the hydroxy groups in the carbohydrate is replaced with hydrogen, halogen, amino, $C_1$–$C_4$ alkoxy or $C_1$–$C_4$ alkyl group. Exemplary modified carbohydrate moieties include, 5-deoxyglucose, glucosamine, 2,3-dideoxyglucose, 2-fluoroglucose, 5-fluoroglucose, 3-methyl-3-deoxyglucose, 2-methoxy glucose, 2,3-O-isopropylidene glucose, 2-acetylglucose, 2,3-diacetylglucose, and 2,3-difluoroglucose.

Substituents $R_1$ and $R_2$ can independently be substituted at the six-membered or the five-membered ring moiety. Preferably, $R_1$ and $R_2$ are substituted at the six-membered ring moiety. Preferably, $R_1$ and $R_2$ are independently H, $OR_4$, $SR_5$, $NR_6R_7$, $C_1$–$C_4$ alkyl, or halogen. Alkyl groups according to the invention are aliphatic hydrocarbons which can be straight or branched chain groups. Alkyl groups optionally can be substituted with one or more substituents, such as halogen, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, trifluoromethyl, chloromethyl, trichloromethyl, and pentafluoroethyl. More preferably, at least one of $R_1$ and $R_2$ is H, and most preferably $R_1$ and $R_2$ are H.

X is O, S, or $NR_3$. Preferably, X is $NR_3$. $Z_1$ and $Z_2$ are H, $OR_8$, $SR_9$ or $NR_{10}R_{11}$. Preferably $Z_1$ is $OR_8$. Preferably $Z_2$ is H or $SR_9$.

$R_3$, $R_4$, $R_5$, $R_6$ and $R_7$ are independently H or $C_1$–$C_4$ alkyl. Preferably $R_3$ is H.

$R_8$, $R_9$, $R_{10}$, and $R_{11}$ are independently H, or a saccharide moiety. Preferably $R_8$ is a monosaccharide or a disaccharide moiety, more preferably $R_8$ is β-D-glucopyranosyl or β-D-glucopyranosyl (1–6)-β-D-glucopyranosyl moiety. Preferably $R_9$ is a monosaccharide moiety, more preferably β-D-glucopyranosyl.

Particularly preferred compounds of the present inventions include 3-O-β-D-glucopyranosyl(1–6)-β-D-glucopyranosylindole and 2-S-β-D-glucopyranosyl-3-O-β-D-glucopyranosyl-2-mercaptoindole.

The compounds of the present invention can be isolated from Calanthe discolor Lindl. For example, a method for preparing an extract from Calanthe discolor Lindl. and uses hereof as a hair growth promoter are disclosed in U.S. patent application Ser. Nos. 08/661,970 and 08/167,828. Alternatively, the compounds of the present invention can be synthesized from readily available starting materials.

Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be. oxidized to form ketones. Thus, substitution or alteration reactions can be employed to provide a variety of substituents throughout the molecule of the starting material, intermediates, or the final product, including isolated products.

The compounds of the present invention have a variety of physiological properties including increasing blood flow, promoting hair growth and whitening of skin. These physiological properties can be elicited by administering the compound topically, orally, or parenterally. The compound can be administered directly or it can be admixed with a suitable pharmaceutical carrier (i.e., vehicle). A pharmaceutically acceptable vehicle, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Vehicles can also include viscosity enhancing agents, such as sodium carboxymethylcellulose, sorbitol, or dextran. The vehicle will also usually contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations will either be liquid, gel or solids depending on the mode of administration. Thus, in a non-liquid formulation, the vehicle may comprise dextrose, human serum albumin, preservatives, etc., to which sterile water or saline could be added prior to administration.

In another aspect of the present invention, a compound of the present invention is administered to a patient to achieve a desired physiological effect. Preferably, the patient is a mammal, more preferably a human.

Many protocols for administering the compound of the present invention to humans or animals are within the skill of the art. The preferred route to administration is topical. The concentration of the compound is selected so that an effective dose is presented in the host to elicit a desired response. Within wide limits, the dosage is not believed to be critical.

EXAMPLES

Example 1

This example illustrates a method for isolating and characterizing Calanthoside A from Calanthe discolor Lindl.

Fresh rhizome (7.5 Kg) of Calanthe discolor Lindl. was cut into strips and extracted three times with hot MeOH (18 liter). The extracts were combined and concentrated to provide 330 g of methanol extract residue (4.4% yield). This ethanol extract residue was extracted with ethyl acetate (EtOAc) and $H_2O$ (1:1). The aqueous layer was separated and concentrated to yield 225 g (3.0% overall yield) and was subjected to a reverse-phase silica gel chromatography with water-methanol as eluant to obtain 13 g (1.7% overall yield) of a crude material.

The crude material was further purified by silica gel column chromatography using the following eluant system: $CHCl_3$:MeOH (10:1 then 3:1 and then 1:1) followed by $CHCl_3$:MeOH:H2O (65:35:10 (Lower Layer) then 6:4:1) and finally MeOH. Of the eight fractions obtained, fraction 7 (4300 mg, 0.057% overall yield) was further purified by silica gel column chromatography using the following solvent system: $CHCl_3$:MeOH:$H_2O$ (7:3:1(Lower Layer) then 65:35:10 (Lower Layer) and then 6:4:1). Further purification using reverse-phase HPLC using YMC-Pack R&D ODS-5 (250×20 mm i.d.) column and MeCN—$H_2O$ (30/70 v/v) as a solvent followed by another HPLC using MeOH—$H_2O$ (25:75 v/v) as a solvent provided 81.9 mg (0.0011% overall yield) of Calanthoside A as a light yellow non-crystal powder. $[\alpha]_D^{25}$=+164.0° (c=0.01, MeOH). High resolution FAB-MS (m/z) Calc. for $C_{20}H_{28}NO_{11}(M+H)^+$: 458.1638. Found: 458.1650. IR(KBr, $cm^{-1}$): 3490, 1618, 1554, 1458, and 1028. UV (c=0.0006, MeOH, nm (log $\epsilon$)): 282 (4.7), 224 (5.4). $^1$H NMR ($CD_3OD$, 500 MHz, $\delta$): 4.40 (1H, d, J=7.6Hz), 4.74 (1H, d, J=7.3 Hz) 6.97 (1H, ddd, J=1.3, 6.9, 7.9 Hz),7.07 (1H, ddd, J=1.3, 6.9, 8.3 Hz), 7.15 (1H, s), 7.27 (1H, dd, J=1.3, 8.3 Hz), 7.67 (1H, dd, J=1.3, 7.9 Hz). $^{13}$C-NMR ($CD_3OD$, 125 MHz, $\delta$): 138.8, 135.4, 122.8, 121.3, 119.5, 119.6, 112.2, 112.4, 105.4, 104.7, 77.9, 77.9, 77.9, 77.3, 75.1, 75.0, 71.5, 71.5, 69.9, and 62.7. Positive-mode FAB-MS (m/z): 480 $(M+Na)^+$. Negative-mode FAB-MS (m/z): 456 $(M-H)^+$.

Identification of Sugar Moiety

Calanthoside A (3 mg) was dissolved in $H_2SO_4$-dioxane solution (1:1, v/v, 1.0 ml) and was refluxed under nitrogen atmosphere for two hours. The sulfuric acid was neutralized with anion exchange resin IRA-400 (OH-form). The resin was removed by a filtration, and the filtrate was concentrated to provide 2.8 mg of material. The material was purified by reverse-phase silica gel chromatography using $H_2O$—MeOH as eluant to provide 1.0 mg of crude product. The crude product was dissolved in pyridine and L-cysteinyl methyl ester hydrochloride was added and stirred for one hour at 60° C. After which, 0.3 mg of N,O-Bis (trimethylsilyl) trifluoroacetamide was added and stirred for additional one hour at 60° C. The resulting solution was filtered. Analysis of the filtrate using gas chromatography revealed the sugar as D-glucose.

The molecular formula of Calanthoside A was determined to be $C_{20}H_{27}NO_{11}$ by FAB-MS and High resolution FAB-MS. IR spectrum suggested the presences of a hydroxyl group (3490 $cm^{-1}$) and a pyrrol ring moiety (1554 $cm^{-1}$). The presence of two glucose moieties which are β bonded to each other was determined by $^1$H-NMR and $^{13}$C-NMR spectrum analysis. The absolute configuration of glucose was determined by gas chromatography analysis. Glucose-glucose linkage was determined by comparison of $^1$H-NMR and $^{13}$C-NMR spectrum of Calanthoside A with the known compound indican.

From the results of $^{1}$H—$^{1}$H, $^{13}$C-$^{1}$HCOSY, and $^{13}$C-$^{1}$HOHAHA spectrum analysis, the glycosyl signals were completely assigned. The β-bond of the two glucose moieties was determined from the coupling constants of anomeric hydrogen and chemical shift of anomeric carbon. A coupling between anomeric hydrogen of the first glucose moiety, the third carbon of indole ring and the sixth carbon of second glucose moiety was observed in HMBC spectrum. Consequently, Calanthoside A has been determined to be 3-O-β-D-glucopyranosyl (1–6)-β-D-glucopyranosylindole. The chemical structure of Calanthoside A (II) is shown below.

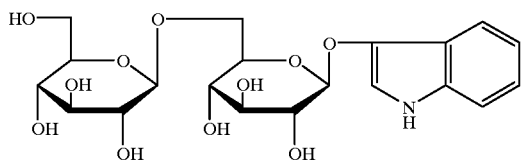

II

Example 2

This example illustrates a method for isolating and characterizing Calanthoside B from Calanthe discolor Lindl. and for preparing Calanthoside B octaacetate.

Crude material, as prepared in Example 1, was further purified by a reverse-phase silica gel column chromatography using 50:50 (v/v) MeOH:H$_2$O then increasing gradually to 80:20 (v/v) Of the eight fractions obtained, fraction 1 was further purified by silica gel column chromatography using the following solvent system as eluant: CHCl$_3$:MeOH:H$_2$O (7:3:1 (Lower Layer)) then gradually increasing to 65:35:10 (Lower Layer) and finally to 6:4:1. Of the eight fractions thus obtained, fraction 5 was further purified by reverse-phase silica gel column chromatography using MeOH:H$_2$O (40:60, v/v) followed by reverse-phase HPLC using YMC-Pack R&D OSD-5 (250×20 mm i.d.) column and MeCN—H$_2$O (25:75 v/v) solvent to obtain Calanthoside B as a light yellow non-crystal powder. $[α]_D^{25}$=+12.0° (c=0.2, MeOH). High resolution FAB-MS (m/z): Calc. for C$_{20}$H$_{28}$NO$_{11}$S(M+H)$^+$: 490.1301. Found: 490.1342. IR(KBr, cm$^{-1}$): 3453, 1620, 1560, 1448, 1043. UV (c=0.0006, MeOH, nm(log ε)): 289(4.0), 221(4.4). $^1$H NMR (CD$_3$OD, 500 MHz, δ): 4.43 ($^1$H, d, J=9.2 Hz), 4.92 (1H, d, J=7.3 Hz), 7.00 (1H, ddd, J=1.2, 7.9, 7.9 Hz), 7.13 (1H, ddd, J=1.2, 7.9, 7.9 Hz), 7.26 (1H, dd, J=1.2, 7.9 Hz), and 7.79 (1H, dd, J=1.2, 7.9 Hz). $^{13}$C NMR (CD$_3$OD, 125 MHz, δ): 142.0, 136.3, 124.2, 120.3, 121.5, 119.5, 113.3, 112.2, 112.2, 89.4, 81.9, 79.1, 78.0, 77.8, 75.4, 73.7, 71.2, 71.2, 62.7, and 62.4. Positive-mode FAB-MS (m/z): 512 (M +Na)$^+$.

Identification of Sugar Moieties

Identification of sugar moieties on Calanthoside B as D-glucose was determined by gas chromatography analysis as described in Example 1.

Analysis of IR spectrum revealed the presence of a hydroxyl group (3453 cm$^{-1}$) and a pyrrol ring moiety (1560 cm$^{-1}$) in Calanthoside B. The peak of pseudo molecular ion was observed at m/z 512 (M+Na)$^+$ by positive mode FAB-MS. Calanthoside B was determined to have the molecular formula C$_{20}$H$_{27}$NO$_{11}$S by High Resolution FAB-MS. The presence of two β-glucose moieties were determined by the coupling constants of anomeric hydrogen and the chemical shift of anomeric carbon. Comparison of $^1$H NMR and $^{13}$C NMR data revealed that glucose structure of Calanthoside B is different from glucose structure of Calanthoside A.

The signals of glucoses were assigned by the analysis of $^1$H—$^1$H, $^{13}$C-$^1$HOHAHA Spectrum. The presence of a long range coupling between the anomeric hydrogen of one of the glucose moieties and the third carbon atom of indole ring in HMBC spectrum and a long range coupling between the anomeric hydrogen of the other glucose moiety and the second carbon atom of indole ring revealed that two glucose moieties are linked to the second and third carbon atoms of the indole ring. In addition, comparison of $^{13}$C NMR data between Calanthoside B and the known compound S-glycoside boreavan A, and N-glycoside PF-P also suggested that a glucose moiety is linked to a second carbon atom of the indole ring. Two-dimensional NMR analysis of Calanthoside B octaacetate also showed a similar correlation. Thus, Calanthoside B was determined to be 2-S-β-D-glucopyranosyl-3-O-β-D-glucopyrannosyl-2-mercaptoindole. The chemical structure of Calanthoside B (III) is shown below.

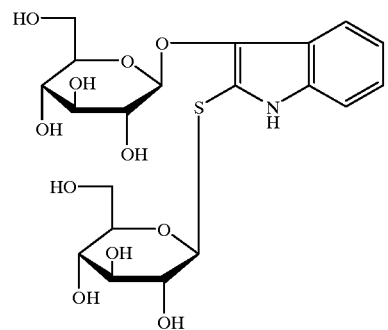

III

Preparation of Calanthoside B octaacetate

Calanthoside B octaacetate was obtained by acetylation of Calanthoside B with acetic anhydride-pyridine.

$^1$H-NMR (CD$_3$OD, 500 MHz, δ): 1.98 (3H, s), 2.03 (3H, s), 2.03 (3H, s), 2.04 (3H, s), 2.08 (3H, s), 2.15 (3H, s), 2.15 (3H, s), 2,20 (3H, s), 7.09 (1H, ddd, J=0.9, 8.2, 8.2 Hz), 7.24 (1H, ddd, J=0.9, 8.2, 8.2 Hz), 7.33 (1H, dd, J=0.9, 8.2 Hz), and 7.73 (1H, dd, J=0.9, 8.2 Hz). $^{13}$C-NMR (CD$_3$OD, 125 MHz, δ) : 20.5, 20.6, 20.6, 20.7, 20.8, 20.9, 21.0, 21.0, 61.6, 62.2, 67.6, 68.6, 70.0, 71.3, 71.8, 74.1, 76.5, 83.7, 102.7, 110.8, 111.1, 119.0, 119.9, 120.8, 123.8, 135.1, and 141.0. The chemical structure of Calanthoside B octaacetate (IV) is shown below.

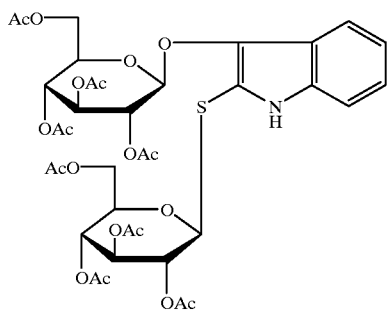

IV

Example 3

This experiment illustrates ability of Calanthoside A to promote skin blood flow.

Wistar male rats (180 to 200 g weights) were employed as experimental animals. The quantity of the skin blood in this experiment was measured with a Laser Doppler Flowmeter (PF2B, Perimed). The backs of rats were sheared. A day later, the rats were anesthetisized with urethane (1 g/Kg) and a quantity of blood flow was measured. This quantity was defined as a normal flow.

Immediately after the measurement of the normal flow, a group of rats were treated with topical application of 25 µl of test liquid in 50% ethanol solution and a group of rats were treated with topical application of 50% ethanol solution as a control. The skin blood flow was measured at 20 minute, 40 minute and 60 minute intervals. MeOH extract from Calanthe discolor Lindl. (CDM-ext: 0.5% and 2.0%), Calanthoside A (0–20%), and indilbin (0.2%) were tested, and the results for the extract are shown in Table 1.

TABLE 1

| Process | Applied Quantity | Blood Flow Increase (%) 20 min. | 40 min | 60 min |
|---|---|---|---|---|
| Normal | | 4.3 ± 2.5 | 6.6 ± 10.5 | 13.4 ± 10.2 |
| Control | | −0.1 ± 6.2 | 5.3 ± 5.8 | 0.4 ± 4.1 |
| Extract | 0.5% | 30.1 ± 6.6 | 42.4 ± 7.0 | 46.3 ± 7.0 |
| | 2.0% | 35.6 ± 8.5 | 44.6 ± 10.3 | 62.3 ± 11.8 |

Both 0.5% solution and 2.0% solution of MeOH extract increased skin blood flow of the rats. Calanthoside A increases skin blood flow when measured after 20 minutes. The ability of Calanthoside A to increase skin blood flow can be used to promote hair growth.

Example 4

This experiment illustrates ability of Calanthoside B to promote skin blood flow.

The procedure of Example 3 was used using 0.2% Calanthoside B. Calanthoside B increases skin blood flow when measured after 20 minutes. The ability of Calanthoside B to increase skin blood flow can be used to promote hair growth.

Example 5

This experiment illustrates ability of Calanthoside A to whiten skin by reducing the activity of tyrosinase, which is active in the production of melatonin.

This experiment was conducted according to the procedure of Manson and Peterson. A 0.5 ml L-Dopa solution (0.03% in pH6.8 PBS) was added to 0.5 ml of a test liquid, and incubated for 5 minutes at 25° C. After which, a 0.5 ml of tyrosinase solution (obtained from a mushroom) was added and the mixture was further incubated for 5 minutes at 25° C. Absorbance (D1) of the resulting mixture was measured at 475 nm. The same experiment without L-Dopa solution was conducted and the absorbance (D2) was measured. Absorbance (D3) of Dopachrome without test liquid was also measured. The percent inhibition of enzyme-complex formation, which is defined as an index for activation of tyrosinase, was determined from D1, D2 and D3 using the following formula:

$$\% \text{ Inhibition} = \frac{[D3 - (D1 - D2)]}{D3} \times 100$$

The MeOH extract from Calanthe discolor Lindl. (CDM-ext), the EtOAc Partition Phase, $H_2O$ Partition Phase and Calanthoside A were used as test liquids. Kojic acid was used for a positive control test. The results are shown in Table 2.

TABLE 2

| Test Liquid | Concentration (µg/ml) | Absorbance (× 1,000) | % Inhibition |
|---|---|---|---|
| Normal (D3) | | 708.0 ± 2.1 | |
| MeOH Extract | 50 | 675.2 ± 3.3 | 4.6 |
| (CDM-ext) | 200 | 551.8 ± 12.8 | 22.1 |
| (D1–D2) | 500 | 418.7 ± 16.3 | 40.9 |
| | 1,000 | 371.0 ± 3.0 | 47.6 |
| | 2,000 | 306.0 ± 3.5 | 56.8 |
| Kojic Acid | 5 (µM) | 478.0 ± 3.1 | 32.5 |
| (Control) | 20 (µM) | 240.7 ± 3.5 | 66.0 |
| (D1–D2) | 50 (µM) | 122.8 ± 1.7 | 82.7 |
| Normal (D3) | | 732.8 ± 2.9 | |
| EtOAc partition | 50 | 652.2 ± 3.8 | 11.0 |
| layer | 200 | 511.5 ± 0.6 | 30.2 |
| (D1–D2) | 500 | 364.2 ± 4.1 | 50.3 |
| $H_2O$ partition | 5 (µM) | 630.7 ± 0.9 | 13.9 |
| layer | 20 (µM) | 408.5 ± 2.1 | 44.3 |
| (D1–D2) | 50 (µM) | 235.8 ± 4.2 | 67.8 |
| Kojic Acid | 5 (µM) | 526.0 ± 2.6 | 28.2 |
| (Control) | 20 (µM) | 276.8 ± 1.9 | 62.2 |
| (D1–D2) | 50 (µM) | 144.3 ± 2.0 | 80.3 |
| Normal (D3) | | 740.0 ± 6.6 | |
| Calanthoside A | 50 | 454.0 ± 0.0 | 38.6 |
| (D1–D2) | 200 | 252.0 ± 0.0 | 65.9 |
| Kojic Acid | 5 (µM) | 562.8 ± 2.0 | 23.9 |
| (Control) | 20 (µM) | 301.5 ± 1.5 | 59.3 |
| (D1–D2) | 50 (µM) | 158.7 ± 1.2 | 78.6 |

As shown in Table 2, as the amount of MeOH extract, EtOAc partition layer, and $H_2O$ partition layer increases the antityrosinase activity increases. The positive control, kojic acid, also shows strong anti-tyrosinase activity.

The whitening effect of Calanthoside A can be used for cosmetic purposes.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for increasing blood flow to the skin, wherein said method comprises administering a composition comprising a compound selected from the group consisting of 3-O-β-D-glucopyranosyl(1-6)-β-D-glucopyranosyl indole, 2-S-β-D-glucopyranosyl-3-O-β-D-glucopyranosyl-2-mercaptoindole, and mixtures thereof.

2. The method of claim 1, wherein the composition is topically administered.

3. The method of claim 1, wherein the composition is orally administered.

4. The method of claim 1, wherein the composition further comprises a pharmaceutically acceptable carrier.

5. A composition comprising;
  (a) a compound selected from the group consisting of 3-O-β-D-glucopyranosyl(1-6)-β-D-glucopyranosyl indole, 2-S-β-D-glucopyranosyl-3-O-β-D-glucopyranosyl-2-mercaptoindole, Calanthoside B octaacetate and mixtures thereof; and
  (b) a pharmaceutically acceptable carrier.

* * * * *